US009506856B2

(12) United States Patent
Krief (10) Patent No.: US 9,506,856 B2
(45) Date of Patent: Nov. 29, 2016

(54) OPTICAL DEVICE FOR DETECTING ABNORMALITIES IN MILK

(71) Applicant: DELAVAL HOLDING AB, Tumba (SE)

(72) Inventor: Haim Krief, Tumba (SE)

(73) Assignee: DELAVAL HOLDING AB, Tumba (SE)

( * ) Notice: Subject to any disclaimer, the term of this patent is extended or adjusted under 35 U.S.C. 154(b) by 0 days.

(21) Appl. No.: 14/427,000

(22) PCT Filed: Sep. 27, 2013

(86) PCT No.: PCT/SE2013/051125
§ 371 (c)(1),
(2) Date: Mar. 10, 2015

(87) PCT Pub. No.: WO2014/055011
PCT Pub. Date: Apr. 10, 2014

(65) Prior Publication Data
US 2015/0241336 A1    Aug. 27, 2015

Related U.S. Application Data

(60) Provisional application No. 61/708,087, filed on Oct. 1, 2012.

(30) Foreign Application Priority Data

Oct. 1, 2012  (SE) ...................................... 1251098

(51) Int. Cl.
*G01N 21/25* (2006.01)
*A01J 5/013* (2006.01)
(Continued)

(52) U.S. Cl.
CPC .............. *G01N 21/25* (2013.01); *A01J 5/0135* (2013.01); *G01N 33/04* (2013.01); *G01N 33/14* (2013.01)

(58) Field of Classification Search
CPC .............. G01J 3/51; G01J 3/02; G01J 3/513; G01J 3/2803; G01J 3/46

USPC ........................................................ 356/419
See application file for complete search history.

(56) References Cited

U.S. PATENT DOCUMENTS 5,012,762 A    5/1991  Moskvin
6,793,624 B2   9/2004  Tsenkova
(Continued)

FOREIGN PATENT DOCUMENTS

BY    13970 C1       2/2011
DE    27 59 126 A1   7/1979
(Continued)

OTHER PUBLICATIONS

International-Type Search Report, dated May 24, 2013, from corresponding PCT application.
(Continued)

*Primary Examiner* — Tarifur Chowdhury
*Assistant Examiner* — Md M Rahman
(74) *Attorney, Agent, or Firm* — Young & Thompson (57) ABSTRACT

An method and system for detecting color changes in fluids detects the color intensities, and includes a white light emitter and a detector that generates signals representing the detected intensity of red, blue, green, and white light. A processor receives the generated signals and calculates values representing the ratio of detected red to white light, blue to white light, and green to white light. The processor further compares the calculated ratios with reference values and generates a signal when the results of the comparison indicate that the ratios differ from the reference values. By generating the ratio of intensity of each received color to the intensity of received white light, the values are rendered virtually self-compensating and thus largely insensitive to variations in temperature and in intensity that may occur over time with aging of the components.

20 Claims, 3 Drawing Sheets

(51) Int. Cl.
*G01N 33/04* (2006.01)
*G01N 33/14* (2006.01)

(56) References Cited

U.S. PATENT DOCUMENTS

| | | | |
|---|---|---|---|
| 8,499,717 B2 | 8/2013 | Birk et al. | |
| 2003/0065480 A1* | 4/2003 | Vijverberg | A01J 5/007 702/182 |
| 2005/0209796 A1* | 9/2005 | Kolosov | G01N 11/16 702/52 |
| 2010/0123695 A1* | 5/2010 | Hong | H05B 33/0869 345/207 |
| 2010/0326359 A1* | 12/2010 | Gudmundsson | A01J 5/041 119/14.01 |
| 2011/0025826 A1* | 2/2011 | Dabiri | G01P 5/001 348/46 |
| 2012/0050307 A1* | 3/2012 | Mahowald | H05B 37/0218 345/590 |
| 2012/0257821 A1* | 10/2012 | Saito | G06T 3/4015 382/162 |
| 2012/0280624 A1* | 11/2012 | Baaijens | A47F 11/10 315/149 |

FOREIGN PATENT DOCUMENTS

| | | |
|---|---|---|
| EP | 1 000 535 A1 | 5/2000 |
| EP | 1 297 743 A2 | 4/2003 |
| EP | 1 297 744 A2 | 4/2003 |
| RU | 2 249 199 C2 | 3/2005 |
| RU | 2 340 171 C2 | 12/2008 |
| SU | 1402304 A1 | 6/1988 |
| SU | 1720601 A1 | 3/1992 |
| WO | 98/30084 A1 | 7/1998 |
| WO | 01/56369 A1 | 8/2001 |
| WO | 02/084260 A1 | 10/2002 |
| WO | 02/093167 A1 | 11/2002 |

OTHER PUBLICATIONS

International Search Report, dated Jan. 30, 2014, from corresponding PCT application.
Supplementary International Search Report, dated Jan. 22, 2015, from corresponding PCT application.

\* cited by examiner

OPTICAL DEVICE FOR DETECTING ABNORMALITIES IN MILK

TECHNICAL FIELD

The present invention is directed to optical devices capable of detecting colour changes in fluids that are indicative of the presence of contaminants, such as blood. It has particular relevance to optical devices for detecting colour changes in milk in real-time in semi-automatic and robotic milking systems.

BACKGROUND

Milk is a significant foodstuff both as a starting material in numerous products and as a final product. An important part of milk production, is to ensure that the milk is of good quality and, specifically, free from bacteria and other pathogens or contaminants that could have a bearing on its quality. When a diary animal suffers from an infection of the udder, the first outward sign is often a change in the milk. Specifically, milk may contain small quantities of blood, puss or other contaminants that change the colour of the milk. Many national and international regulations stipulate that any such milk be separated and not used for human consumption. In automated milking systems in which teat cups are connected automatically to the teats of an animal, a visual inspection of the milk is impractical, but the need for quality verification and possible separation of milk is of paramount importance to prevent sub-standard milk from being mixed with milk from healthy animals to the detriment of the bulk milk quality.

DE 27 59 126 describes an arrangement for separating milk which includes a light source and photodiode for detecting the colour of milk. When the colour of the milk indicates that it contains blood and puss, the milk is diverted to a separate container. This system, while it may permit some degree of colour change to be determined, cannot provide any great accuracy and consequently caries the risk of sub-standard milk being mixed with bulk milk or good milk being discarded.

WO 98/30084 describes an automatic milking arrangement that is equipped with a colour sensing system that is sensitive to frequency bands for red, green and blue light. The intensity signals from each colour band are compared mutually and with reference values to determine a change in colour. The reference values may be an average of recently determined values for each animal at a number of previous milking runs or a common value obtained from the milk of all animals. While this system enables a change of colour to be determined more accurately by virtue of the different colours detected, it nevertheless requires careful calibration to maintain this accuracy and to compensate for changes in temperature and aging of the various components, which ultimately makes it difficult to use reliably in practice.

It is an object of the present to overcome the problems of the prior art and provide a sensor arrangement that can detect a colour change indicative of the presence of certain contaminants in milk, milk products and other fluids and that is inherently accurate and reliable over time.

SUMMARY

This and further objects are achieved in an arrangement for detecting colour changes in fluids, in a milking arrangement, in a milk meter and in a method of detecting colour variations in fluids as defined in the appended claims.

More specifically, in accordance with one aspect of the present invention an arrangement for detecting colour changes in fluids is proposed that comprises an optical arrangement for detecting the intensities of certain colour frequencies in a fluid, the optical arrangement being arranged for coupling to a container adapted to carry a fluid. The optical arrangement includes a white light emitter and a detector arranged to detect light from fluid contained in the container and to generate signals representing the detected intensity of red light, blue light, green light and white light. The optical arrangement further includes a processor connected to the detector and arranged to receive the signals and to calculate values representing the ratio of detected red light to detected white light, the ratio of detected blue light to detected white light and the ratio of detected green light to detected white light. The processor is further arranged to compare the ratios obtained with reference values and to generate a signal when the results of the comparison indicate that the ratios differ from the reference values.

By generating the ratio or fraction of the intensity of each received colour to the intensity of received white light, the values are rendered virtually self-compensating and thus largely insensitive to variations in temperature and in intensity that may occur over time with aging of the components. Calibration is thus very simple or even unnecessary, depending on the accuracy required.

The optical arrangement can be coupled to a container that contains fluid. For the purposes of this document, the term, "container" is intended to designate any vessel, receptacle or conduit capable of retaining or guiding fluid and encompasses sample chambers or cups as well as pipes or hoses or dips or pockets within conduits that are designed to retain a portion of fluid passing through the conduit. Consequently the fluid tested in this way may be held substantially stationary in the container, or may be in motion, flowing through the container or held temporarily by the container.

Preferably, the processor is arranged to compare the ratios with reference values, such as reference values obtained from a reference fluid sample or previous fluid samples taken from the same or different sources. These reference values may be individual values for each colour ratio, or a range of values outside of which the generated ratios are indicative of the presence of a contaminant in the fluid, such as blood or puss in milk.

In a preferred embodiment, the white light emitter and the detector are arranged side by side, such that light emitted by the emitter will be reflected by milk in the container and detected by the detector. By detecting reflected light as opposed to absorbed or transmitted light, the measurement can be performed on any thickness of fluid and is thus largely independent of the diameter of the container containing the fluid and the quantity of fluid flowing through it or held in it.

In a particularly advantageous arrangement, the white light emitter is a wide-angle light emitter, preferably a wide-angle LED. This allows reflected signals to be detected by the detector even when the light emitter and detector are arranged very close to one another. The overall size of the optical arrangement can thus be very small, which means that it can be built-in to various different containers, such as milk lines, milk meters or teat cups of a milking arrangement, other lines or containers in a processing plant for fluid foodstuffs or even cartons or packaging containing fluids. This size advantage is further enhanced, when the emitter and detector are arranged on the same side of a printed circuit board.

Whilst the use of intensity ratios to determine the proportion of each colour in a fluid means that any change in these ratios is less sensitive to temperatures changes, a minimal variation with temperature will be present. In order to obtain a particularly accurate determination of colour change so as determine the presence of very small concentrations of contaminants it can, therefore, be advantageous to provide a temperature sensor arranged on the same side of the printed circuit board for measuring the ambient temperature around the white light emitter and the detector and thus provide information of the operating temperature of these components. The measured temperature can then be used to correct the ratio values.

In a particularly advantageous embodiment of the present invention, the detector comprises an array of detecting elements, the array including at least one element arranged to detect red light, at least one element arranged to detect green light, at least one element arranged to detect blue light and at least one element arranged to detect white light. Preferably the array contains an equal number of red, blue, green and white light detecting elements to ensure an even spread and distribution of detected colour.

It is preferable when each detecting element comprises a photodiode arranged to detect white light, and wherein the at least one red detecting element further comprises a red filter, the at least one green detecting element further comprises a green filter and the at least one blue detecting element further comprises a blue filter. By using the same base component for each detecting element, namely a photodiode for detecting white light, the components will have the same electrical characteristics and these characteristics will tend to alter in the same manner with age. This contributes to the self compensating nature of the colour change detecting arrangement over time.

It is also advantageous when an infrared filter is placed before all detecting elements but particularly before the detecting elements for red and white light to remove spurious signals that may be caused by sunlight impacting on the fluid or its container.

In a preferred embodiment of the invention, the detector further includes at least one amplifier arranged to amplify the signal received from each detecting element, at least one integrator arranged to integrate the signal received from each detecting element and at least one analog-to-digital converter arranged to digitise the signal received from each detecting element, and wherein the processor is arranged to vary at least one of the amplification of said amplifiers and the integration time of said integrators to modify the dynamic range of said detector. The integration time is equivalent to the exposure time of the detector to the illuminated fluid. The ability to vary the amplification and/or exposure or integration time applied to each colour intensity signal means that the optical arrangement can be adjusted to respond optimally in any system and situation without needing to alter the intensity of illumination.

The arrangement in accordance with this invention is suitable for detecting colour changes in any fluid, but is particularly suitable for detecting colour changes in fluid foodstuffs to determine the presence of contaminants therein and of particular advantage when used for detecting colour change in milk or products derived from milk to infer the presence of blood, puss or other constituents that signal a health problem or degradation of quality. The container for carrying fluid is thus preferably arranged to carry milk, whether in the form of a conduit, transporting milk between two points or a receptacle holding milk at least temporarily.

In a further embodiment of the present invention, the arrangement for detecting colour changes is incorporated in a milking arrangement and used to detect colour changes in milk. This arrangement comprises a plurality of teat cups for connecting to the teats of an animal with at least one milk line for transporting milk from the teat cups to a storage container. In this case, the container to which the optical arrangement is coupled may be the teat cup, a portion of the milk line or even a storage container, such as a collecting jar. The advantage of incorporating the arrangement for detecting colour changes in a milking arrangement to monitor milk is that an indication of the quality of the milk can be obtained immediately, i.e. in real time, during the flow of milk or while this milk is in a collection jar. This permits the system to alert the farmer to a potential health problem in the herd and also allows the farmer to separate this milk so that it does not contaminate the bulk milk and have an impact on the overall milk production quality.

Preferably, the milking arrangement comprises a milk meter connected to the milk line, and the arrangement for detecting certain substances in milk is comprised in the milk meter. This has the further advantage of enabling detection of a colour change substantially at the start of milk flow. Using this arrangement, it is possible also to determine the quality of milk from a signal udder portion, i.e. emanating from a single teat. Thus any injury or infection can be identified and reported early and also the loss of milk minimised when mastitis is present in not all udder portions.

In order to protect the quality of milk produced by one or more animal, it is particularly advantageous when the milking arrangement comprises a controller arranged to communicate with the processor and arranged to control a milk separation mechanism, wherein the controller is arranged to control the milk separation mechanism to separate milk in response to the signal generated by the processor. Any milk that may be sub-standard can thus be separated from bulk milk virtually at source and fully automatically to prevent mixing and thus potential contamination of the remaining milk.

In a further advantageous embodiment, the milking arrangement further comprises animal identification means arranged to communicate with the controller, wherein the controller is further arranged to store data relating to each identified animal including data relating to the colour of milk from said animals. Thus, the results of the colour analysis are stored alongside other data relating to an animal, such as milk yield, lactation stage, age, treatment, etc so that the farmer can determine how often a colour change has occurred and whether this is related to an injury or infection.

In accordance with a further aspect of the present invention, the arrangement for detecting colour changes in fluids is comprised in a milk meter. Since milk meters already provide data on the flow of milk and in some cases on the quality of milk, it is advantageous both in terms of the required connections and the ease of installation to incorporate the colour sensor arrangement in this device.

Preferably, the milk meter comprises at least one channel for carrying milk and a window located above said channel, wherein the optical arrangement is arranged adjacent the channel over the window for detecting colour changes in milk carried in the channel. The at least one channel may be a tube of essentially uniform cross-section or may constituted by or provided with some kind of retaining means arranged to retain a portion of the milk flowing through the milk meter.

In accordance with a further aspect of the present invention, there is proposed a method for detecting colour variations in fluids which comprises the steps of illuminating fluid contained in a container with white light, detecting light from said fluid and determining an intensity of red light, an intensity of blue light, an intensity of green light and an intensity of white light, determining a first ratio of the detected intensities of red light to white light, a second ratio of the detected intensities of blue light to white light and a third ratio of the detected intensities of green light to white light, comparing these ratios with reference values and generating a signal when the ratios differ from the reference values.

As mentioned above, generating a ratio for each colour frequency intensity to the intensity of white light and using this ratio to determine a change in colour enables the method to be virtually self-compensating and thus less sensitive to temperature and emitter intensity variations.

Preferably, the step of detecting light from the fluid includes detecting light reflected from the fluid. The advantage of detecting light reflected from the fluid is that the thickness of the fluid tested is not critical, in contrast to transmission methods, where the absorption of light depends on the thickness off the liquid sample. Similarly using reflected light also means that the sensor arrangement can be used on both stationary and flowing fluid, for example milk in a milk tube, as well as on any other milk product substance.

Advantageously, the method includes the step of comparing the ratios with a reference value obtained from a reference milk sample or one or more previous fluid samples from the same or different sources. When the fluid to be tested is milk, this means milk from the same animal, the same herd or a range of different animals. By comparing like with like, it is possible to exclude colour variations that may be due to differences in location or production or farming practices as well as feed given to animals. This thus makes it easier to identify changes in colour that are due to specific contaminants, such as blood or puss, that indicate an injury or infection of the dairy animal and which are deleterious to the quality of the milk.

The determination of a significant colour change is preferably achieved by comparing the ratios with a reference range, wherein the step of generating a signal includes generating a signal when the ratios fall outside of the reference range. This permits a certain tolerance in the variation in colour from production run or milking run to the next, for example, and so avoids false positives when minimal colour change occurs naturally, for example with seasonal changes, different feeding habits and possibly lactation stage of dairy animals.

The method is particularly advantages when used in a milking arrangement to identify colour changes in milk during milking or just after milking. The method thus preferably includes the step of connecting teat cups to the teats of an animal and milking the animal, wherein the illuminating step includes illuminating milk flowing through one or more milk tubes connected to the teat cups and further including the step of automatically discarding milk when the comparison step indicates that the ratios differ from the reference values.

The overall management of a dairy herd can be improved when information on any detected colour change is associated with the respect animal and stored for later consultation. In a preferred embodiment, therefore, the method further includes the step of obtaining a unique identity for each animal and storing data on the results of the comparison step in conjunction with the unique identity.

BRIEF DESCRIPTION OF THE DRAWINGS

Further objects and advantages of the present invention will become apparent from the following description of the preferred embodiments that are given by way of example with reference to the accompanying drawings. In the figures:

FIG. 3 is a schematic of the detector in the colour sensor.

DETAILED DESCRIPTION

In the following example, an arrangement for detecting colour changes in fluids is described with reference to its application in a milking system. It will be understood however, that the arrangement is equally applicable to other systems, such as production plants, or even to packaging used both for milk and for other fluid foodstuffs, for example. In the following description the term "arrangement for detecting colour changes" is used interchangeably with the term "optical sensor" and both designate the same arrangement.

Figure 1:
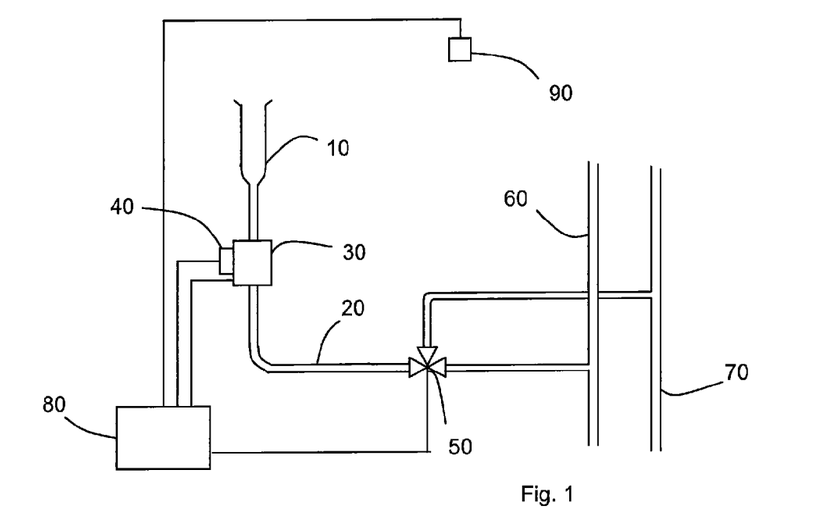
FIG. 1 shows a schematic representation of part of a milking system for milking animals with an arrangement for colour sensor, FIG. 2 schematically illustrates the structure of the colour sensor in operation.

Turning now to FIG. 1 there is shown a representation of part of a milking system for milking dairy animals that is equipped with a colour sensing arrangement according to the present invention. In the figure there is shown a teat cup 10 for connecting to the teat of an animal, which is coupled to a milk line 20. Only one teat cup 10 is illustrated in the figure for reasons of clarity, however, it will be understood that teat cups are present for all teats of the animals to be milked, each teat cup 10 being coupled to a separate milk line 20. A milk meter 30 for measuring the flow and quantity of milk collected by teat cup 10 is connected to each milk line 20. Milk meters of the type illustrated that are capable of determining the start of milk flow and the rate flow of milk and/or the quantity of milk are well known to those skilled in the field of milking so the configuration and operation of this device will not be described further here. In the illustrated embodiment, the milk meter 30 is provided with an optical sensor 40 capable of determining a colour change in the milk. This sensor will hereinafter be referred to as a colour sensor. More specifically, the milk meter 30 is provided with a passage or chamber (not shown) that communicates with the milk line 20 upstream and downstream of this milk meter and through which milk can flow. At one location, an aperture or window 310 (see FIG. 2) is provided, which is of a clear transparent material, such as glass or plastic that allows the passage of visible light with minimum attenuation. The colour sensor 40 is arranged outside this passage over this window 310 and detects the colour of milk contained in this passage. While it is possible to provide the milk meter with an essentially clear transparent wall to enable the milk to be visible from the outside, such an arrangement allows surrounding light to illuminate the milk, which complicates the processing of the colour sensor data. In the illustrated embodiment, the colour sensor 40 is connected to, or integrated in, the wall of the milk meter in such a way that it completely covers the window 310 and thus excludes all external light. The milk meter 30 is connected to a controller 80, which is preferably a computer with associated memory, input means, such as a keyboard, mouse and/or touch screen and output means such as a display, a printer and the like. The controller 80 may be provided by a number of computers connected together, or a single computer, possibly connected to a communications network, such as a LAN, WAN or the Internet. In the illustrated embodiment, two lines are shown between the milk meter 30 and the controller 80, which represent wireless or wired connections. For illustrative purposes, one of these connections is between the body of the milk meter 30 and controller 80 and represents the exchange of data concerning the milk meter function, such as milk flow and milk speed data. The other line is between the controller 80 and the colour sensor 40, which represents the exchange of data concerning the colour sensing of the milk. It will be understood, that when the colour sensor 40 is integrated in the milk meter 30, this exchange of data may occur over a common wired or wireless connection.

In operation, the controller 80 receives milk speed and/or quantity data from the milk meter and data indicative of the colour or colour change of milk from the colour sensor 40. The controller 80 also sends control information to the colour sensor 40 to control the operation of the colour sensor 40 only when milk is flowing through the milk meter 30, based on data received from the milk meter or possibly from the milking system. The controller may also modify various parameters of the colour sensor operation as will be described below. Controller 80 is further connected via a wired or wireless connection to an identification device 90. The identification device 90 interrogates not shown transponders carried by the dairy animals as they enter a milking parlour to obtain a unique identification code assigned to the animal. This identification code enables the controller to uniquely assign and store data relating to the milk yield, milk quality and health to each animal that is milked. Downstream of the milk meter 30, the milk line 20 is connected to a three-way valve 50. This valve 50 has two outputs, one connected to a bulk milk line 60 which carries milk from all teat cups 10 to a bulk milk tank (not shown), possibly via an intermediate collection jar. The other output is connected to a separator tank line 70 which directs any sub-standard milk to a separator tank for subsequent disposal. The controller 80 controls the operation of the 3-way valve 50 via a wired or wireless connection.

As mentioned above, the arrangement described with reference to FIG. 1 will include teat cups for the remaining two or four teats of the animal to be milked. Similarly, the milk line 20, milk meter 30, colour sensor 40 and 3-way valve 50 will also be provided for each separate teat cup. This arrangements permits milk from each teat or udder quarter to be examined separately, and if necessary separated. This prevents sub-standard milk from contaminating healthy milk, but also allows an isolated infection or an injury in one or more teats to be identified and, if necessary, notified to the farmer via printout, by storing the details of the animal in question in a report file for consultation later or by emitting an audible or visible alert signal. Since an udder infection can be very costly, both in terms of treatment and lost milk, it is advantageous when any infection is identified early and treated promptly.

Figures 2, 3:
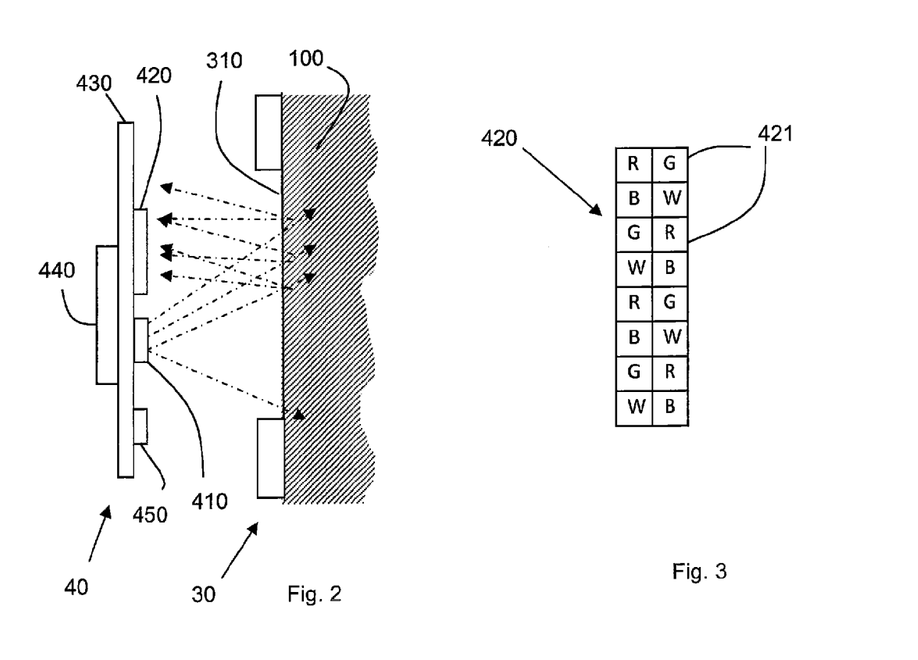

The structure and operation of the colour sensor 40 will now be explained with reference to FIGS. 2 to 4. FIG. 2 shows a cross-sectional view of the colour sensor 40 in position attached to the milk meter 30 opposite the window 310. The colour sensor 40 includes a detector 420 placed adjacent an emitter 410 on a PCB 430. The emitter 410 emits white light and is preferably constituted by a wide-angle LED operating over the entire visible spectrum, i.e. over the wavelength range of 400 nm-700 nm. As illustrated by the dashed lines in FIG. 2, light emitted from the emitter 410 is reflected off the milk 100 flowing through the milk meter aperture 30. The advantage of detecting reflected light rather than transmitted light means that the thickness of the milk in the milk meter 30 or milk line 20 is not critical. By virtue of the wide angle LED, light is spread over a wide area and consequently, even when the LED is positioned very close to the detector 420, sufficient light is reflected and received to provide an accurate and reliable detection of intensity and chromaticity. This allows the colour sensor to be reduced in size and the window 310 of the milk meter 30 can likewise be kept small, and is preferably of the order of 20 mm$^2$. The detector 420 and emitter 410 are connected via the PCB to a processor 440 located on the rear face of the PCB 430. The processor 440 is preferably constituted by a microprocessor and includes associated program and data memory to process signals coming from the detector and control the operation of the emitter 410. A temperature sensor 450 is also provided on the PCB 430 and connected to processor 440 to provide information about the ambient temperature of the components 410, 420 and hence enable adjustment of the various values to changes in temperature, if necessary.

The structure of the detector 420 is shown in more detail in FIG. 3. The detector includes a number of separate detector elements 421, which are preferably constituted by photodiodes 422 (see FIG. 4). Each detector element 421 is arranged to detect a specific frequency band within the visible light spectrum. More particularly, some of the detector elements, marked "R" in FIG. 3, detect only the intensity light in the red spectrum, some detector elements, marked "B" in FIG. 3, detect only blue light, some detector elements, marked "G" in FIG. 3, detect only green light while the remaining detector elements, marked "W" in FIG. 3 detect white light, i.e. a frequency band that covers the whole visible spectrum of 400 nm to 700 nm and thus also the red, blue and green spectrum. The detector elements 421 are arranged in an array that is preferably two-dimensional with the different red, green, blue and white light detector elements 421 distributed evenly throughout this array to ensure a precise and well spread reading of the intensity and chromaticity of light. For the same reason, the detector 40 preferably includes the same number of red, green, blue and white light detector elements 421. In the exemplary embodiment shown in FIG. 3, the detector includes 16 detector elements 421 in an eight-by-two array. However, it will be apparent to those skilled in the art that the detector elements 421 may be arranged in a different array structure in order to suit the particular application and location it is used in.

Figure 4:
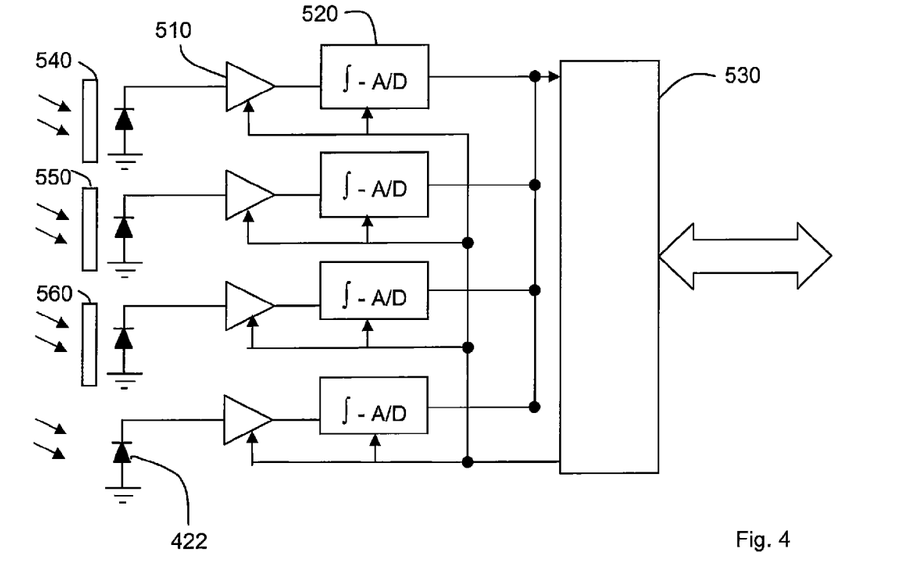
FIG. 4 is a block diagram depicting the functional arrangement of a detection part of the colour sensor.

The electrical arrangement of the detector 420 is illustrated in FIG. 4. As shown schematically in FIG. 4, four photodiodes 422 serving as detector elements 421 are illustrated to the left of the figure. These four photodiodes 422 represent the four groups of R, G, B and W detector elements 421 making up the detector 40. These are each connected to an amplifier 510, which amplifies the signal. The amplified signals are then each integrated and subjected to an analog-to-digital conversion in blocks 520. The digital signals from each block 520 are then sent via an interface 530 to the processor 440. The interface 530 further relays control signals from the processor 440 to the amplifiers 510 and to the integration and A/D functional blocks 520. More specifically, the processor 440, under control of controller 80, is able to adjust the amplification of the signals from each detector element 421 and also to adjust the integration time of the signals. The integration time is essentially the exposure time, so this later adjustment affects the time that the emitter 410 and detector 420 are energised for each reading. In this way, it is possible to obtain a large dynamic range without changing the intensity of the light emitter 410. More specifically, this dynamic range permits blood to be detected in milk at a concentration of as low as 500 ppm up to values of 20,000 ppm. The higher accuracy obtainable with the arrangement according to the present invention means that it is possible to detect an infection or injury of an animal's udder already in the very early stages, thus enabling prompt treatment, while also reducing the risk of contaminated milk being passed and milk of good quality being erroneously rejected.

In a preferred embodiment of the present invention, each detector element 421 includes a photodiode 422 (see FIG. 4) that generates a signal in response to white light, i.e. over substantially all of the visible light spectrum. In order to determine the proportion of incoming light that falls within one of the colours red, green or blue, the detector element 421 for red light also includes a red filter 540, the detector element 421 for green light includes a green filter 550 and the detector element 421 for blue light includes a blue filter 560. The photodiode 422 for the white light detector element 421 has no colour filter or a clear filter (not shown). The use of the same kind of photodiode for each type of detector element 421 ensures that they exhibit similar electrical characteristics, which still further enhances the self-compensating and self-calibrating function of the colour sensor 40. An infrared filter (not shown) may also be placed before the photodiodes to prevent false readings caused by sunlight, particularly of the red and white detector elements 421.

Figure 5:
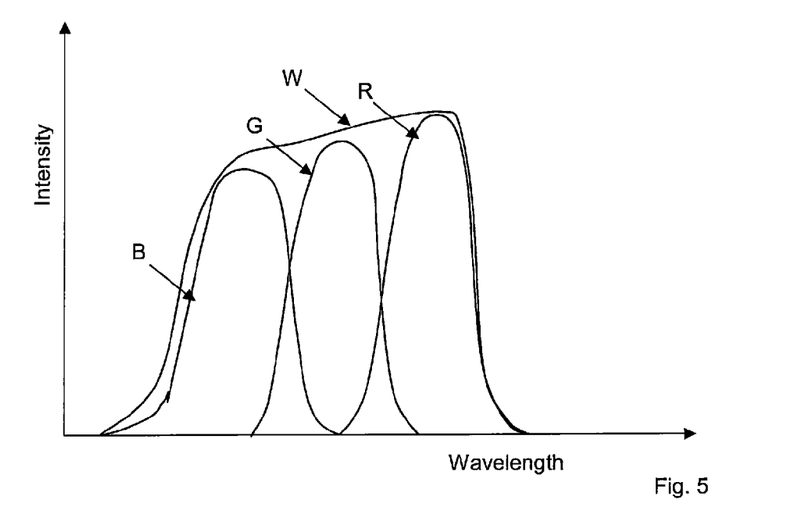
FIG. 5 shows the relationship of signal intensity against wavelength for the four type of detector elements in the colour sensor of the present invention.

FIG. 5 shows the signal response or intensity of each detector element 421 against wavelength. The figure shows four curves labelled W, B, G and R. These curves represent the signal response for each of the detectors for white, blue, green and red light. It is clear that the white light detector element responds to light over the whole of the visible light wavelength range, while the lower wavelengths are detected by red detector element 421, the middle portion of the visible light range is detected by the green detector element 421 and the upper part of the visible wavelength range is detected by the blue detector element 421.

The signals received from the detector 420 are processed in processor 440 in a manner that makes them self-compensating and thus virtually insensitive to temperature changes and aging of the components, particularly of the LED forming the light emitter 410. This is achieved according to the present invention by using the signal from the white light detector elements 421 as a control value. More particularly, the processor 440 divides the value of the amplified, digital signals originating from the red, green and blue detector elements by that originating from the white detector elements. Expressed differently, when the value $R_i$ represents the detected intensity of red light, $G_i$ represents the detected intensity of green light, $B_i$ represents the detected intensity of blue light and $W_i$ represents the detected intensity of white light, the processor calculates the ratio of each of the red, green and blue intensity values to the white intensity value to obtain fraction values for green, $G_f$, red, $R_f$ and blue light, $B_f$ as follows:

$$G_f = \frac{G_i}{W_i}, R_f = \frac{R_i}{W_i}, B_f = \frac{B_i}{W}$$

Because the detector elements 421 have the same ambient temperature and similar electrical properties the fraction values essentially eliminate variations due to temperature changes and the effects of aging. The process of determining colour change is thus rendered far simpler and calibration is also facilitated or even unnecessary.

The self-compensating nature of the fraction values was demonstrated in two experiments, the results of which are shown in Tables 1 and 2 below.

Table 1 shows the results of detected intensity values for the different colours $G_i$, $R_i$ and $B_i$ and the fraction values, $G_f$, $R_f$ and $B_f$ on milk containing 10000 ppm of blood at ambient temperatures of 4° C. and 22° C.

TABLE 1

| Temp [° C.] | $G_i$ | $R_i$ | $B_i$ | $W_i$ | $G_f$ | $R_f$ | $B_f$ |
|---|---|---|---|---|---|---|---|
| 4 | 6961 | 8274 | 5946 | 22603 | 0.308 | 0.366 | 0.263 |
| 22 | 6621 | 7856 | 5649 | 21562 | 0.307 | 0.364 | 0.262 |
| Change [%] | −5.13% | −5.31% | −5.24% | −4.83% | −0.29% | −0.46% | −0.40% |

It can be seen from this table that the intensity values vary by around 5% with the change in temperature of 18° C. while the fraction values vary by only around 0.4%.

Table 2 shows the results of detected intensity values for the different colours $G_i$, $R_i$ and $B_i$ and the fraction values, $G_f$, $R_f$ and $B_f$ at normal intensity of the emitter LED and at a third of normal intensity but constant temperature to simulate the deterioration of the emitter LED over time.

TABLE 2

| Intensity | $G_i$ | $R_i$ | $B_i$ | $W_i$ | $G_f$ | $R_f$ | $B_f$ |
|---|---|---|---|---|---|---|---|
| Normal | 1753 | 1893 | 1916 | 5472 | 0.320 | 0.346 | 0.350 |
| Third | 570 | 605 | 631 | 1777 | 0.321 | 0.340 | 0.355 |
| Change [%] | −67.48% | −68.04% | −67.07% | −67.53% | 0.13% | −1.58% | 1.41% |

In this case, the change in fraction is again very small at less than 2% compared to the change in the intensity values, which show an average change of around 67.5%.

The above experiments demonstrate that the ratios or fraction intensity values within each colour frequency band are essentially self-compensating and thus largely insensitive to both temperature variations and a reduction in intensity of the emitter LED as a result of aging. The effects of any residual variation in intensity over time can be further mitigated by using a reference value or range that is derived from a running average of previously obtained fraction values taken during milking over a fixed period of the previous few days, or weeks for the same animal. Should increased accuracy be required, data on the ambient temperature supplied by the temperature sensor 450 can be used to normalise any readings or calibrate the colour sensor 40.

The colour fraction values obtained from this calculation are then used to determine either an absolute colour in the milk, or a relative change in colour in milk in order to determine whether the milk contains unacceptable levels of contaminants, such as blood or puss. In a preferred embodiment of the invention, this is achieved by comparing the fraction values mutually in order to determine the colour mix detected in the milk, i.e. the proportions of red, blue and green in the reflected light, and comparing the relative proportions with that of normal milk. However, the absolute fraction value could also be compared with a reference level representing a colour mix for normal milk. The level for normal milk, or reference level, may be a fixed stored value, a value obtained from a mix of milk from more than one animal or a value obtained from milk from the same animal as the sample milk. This reference level may also be derived from the average values of a number of samples taken recently, for example the running average of values determined during the last 10 to 20 milking runs so that gradual changes in the milk composition, due to diet, change in lactation period, etc. are largely excluded. The reference level may also be represented by a range of values above and below which the colour is deemed to be abnormal and indicative of the presence of foreign substances. This process is preferably performed in processor 440 but may use data, such as stored reference values or levels received from controller 80. When the reference levels are stored for each animal individually and generated continuously with each new milking sample, it can be advantageous to store these levels as values in the controller 80 or an associated database, in which other data for the animals, such as milk yield, lactation stage, feeding requirements, etc are held and supply these reference values to the processor 440.

Figure 6:
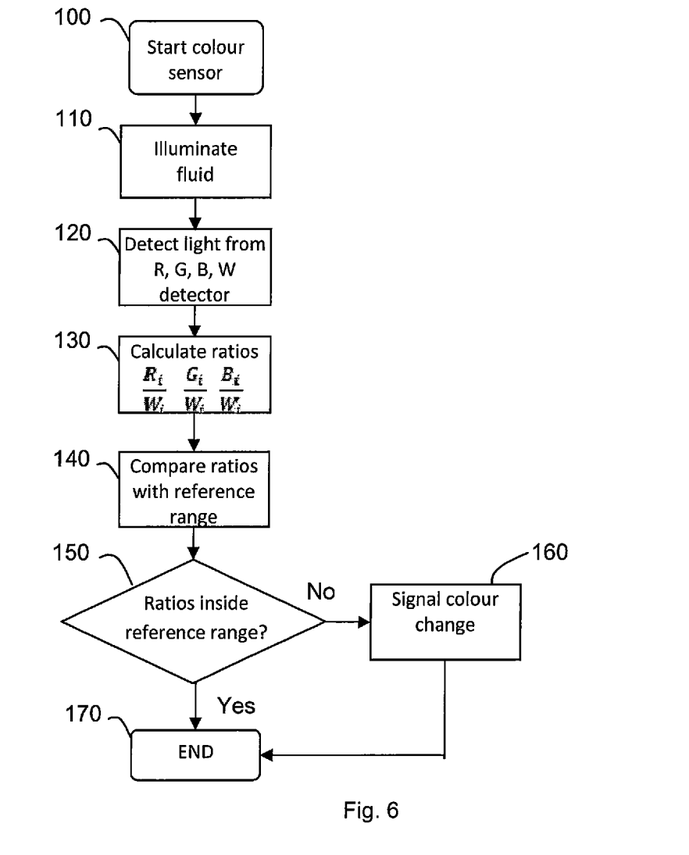
FIG. 6 shows a flow chart illustrating the operation of the colour sensor in accordance with the present invention.

FIG. 6 illustrates the method required to determine a change in colour of a fluid using the colour sensor 40. The method starts at step 100, at step 110 the fluid is illuminated using emitter 410. Simultaneously, the detector 420 detects the intensity of reflected light in the white, red, green and blue spectrums as intensity signals at step 120. At step 130, processor 440 calculates the fraction or ratio values for each of the red, green and blue light intensity values against the white light intensity value. These values are then compared with reference values or ranges, possibly after mutual comparison at step 140. If this comparison shows that the measured values are inside the reference range or ranges at step 150, the method terminates at 170. If, however, the fractions or ratios are outside the reference range or ranges the method passes to step 160 and a signal is generated to that effect, indicating that a change in colour has occurred or that the tested fluid has a non-allowed colour.

When milking of an animal commences, the 3-way valve 50 is in a discharge position, i.e. in a position whereby milk obtained from teat cup 10 and milk line 20 is guided to the separator tank line 70. The animal is identified via the identification device 90, and milking commences under control of controller 80. The colour sensor 40 is controlled by controller 80 to operate when milk is in the milk meter 30, or rather adjacent the window 310. In other words, the operation of the light emitter 410 and detector 420, under control of processor 440, is programmed by controller 80 to synchronise with the presence of milk in the milk meter 30, which in turn is detected and signalled by milk meter 30 to controller 80. When milk flow data is not available, for example when the colour sensor 40 is located elsewhere along the milk line, the colour sensor operation may be synchronised with the application of a pulsation vacuum. Processor 440 analyses data from the detector 420 and sends data representing the detected colour distribution to controller 80 for storage and subsequent processing. When processor 440 determines that the colour of detected milk falls outside of the reference range which could be indicative of the presence of a foreign substance, it also emits a signal to controller 80 indicating this fact. In this case, controller 80 maintains the 3-way valve 50 in the discard position to ensure that milk from the udder portion is not mixed with good milk from the remaining udder portion or portions. Controller 80 also generates an alert message to alert the farmer of the colour reading so that the animal may be checked and, if necessary treated, without delay. The animal may also be separated directly after leaving the milking area, possibly using automatic gates controlled by controller 80. If the colour of the detected milk falls within the reference range, this may also be signalled specifically by processor 440 to controller 80. Controller 80 then switches the 3-way valve 50 to the bulk tank line.

In the embodiment illustrated in FIG. 1, the colour sensor 40 detects the colour of milk flowing through a milk meter 40. Thus the colour sensor is operated only when milk is flowing and thus present in the area adjacent the window 310 of the milk meter 30. In this arrangement the milk meter 30 or rather the passage or chamber through which milk flows serves as a container towards which the colour sensor 40 is directed. However, it is equally possible to position the colour sensor 40 adjacent other containers that hold or guide milk such as elsewhere along the milk line, or even in the teat cup. In this case, the colour sensor 40 may be located adjacent a flow sensor, such as a conductivity or temperature sensor, and operated only when the flow sensor indicates that milk is present. It is furthermore possible to connect the colour sensor to a sample pocket, either provided as a separate chamber into which milk is diverted and remains for a short period of time, or as a pocket in a passage or the milk line, which holds milk temporarily until the milk is replaced by a subsequent flow. In an alternative arrangement, the colour sensor could be coupled to a collector jar, in which milk from one teat or all teats of an animal is collected.

In the above-described embodiment, the colour sensor 40 is used to detect colour changes in raw milk during milking which are indicative of the presence of contaminants, such as blood or puss, and hence provide information on both the quality of the milk and the condition of the cow. However, the colour sensor of the present invention can equally be used to control the quality of other foodstuffs, including products derived from milk, for example to detect contaminants that may be introduced during processing or to determine any change in colour that could signal a deterioration in a product and so provide information on the integrity of sealed packaging and on the safety of consumption of the product. In the latter case, the colour sensor could be provided as a hand-held device or even as a battery-powered element that can be attached to, or built-in to packaging and operated manually, for example by pressing a button.

| List of reference numerals | |
|---|---|
| Teat cup: | 10 |
| Milk line | 20 |
| Milk meter | 30 |
| Colour sensor | 40 |
| 3-way valve | 50 |
| Bulk tank line | 60 |
| Separator tank line | 70 |
| Controller | 80 |
| Identification device | 90 |
| Milk | 100 |
| Milk meter Aperture | 310 |
| Light emitter | 410 |
| Detector | 420 |
| PCB | 430 |
| Processor | 440 |
| Temp sensor | 450 |
| Detector element | 421 |
| Photodiode | 422 |
| Amplifier | 510 |
| Integrator/A/D | 520 |
| Interface | 530 |
| Red filter | 540 |
| Green filter | 550 |
| Blue filter | 560 |

The invention claimed is:

1. A system that detects color changes in a fluid, comprising:

a color sensor (40) that detects fluid color within a container that carries the fluid, wherein the fluid is flowing or stationary milk or a product derived from milk, the color sensor including i) a white light emitter (410) that emits white light into the container and into the fluid carried in the container to thereby illuminate the fluid, wherein the white light illuminates the fluid and is reflected off the fluid as reflected light, ii) a detector (420) that detects the reflected light from the fluid, and generates signals respectively representing a detected intensity of red light, blue light, green light, and white light from the detected reflected light, and iii) a processor (440)

connected to receive the signals respectively representing the detected intensity of red light, blue light, green light, and white light from the detector (420), calculate values representing a) a ratio of detected red light to detected white light, b) a ratio of detected blue light to detected white light, and c) a ratio of detected green light to detected white light, and compare each said ratio with a corresponding reference value to generate a signal when a result of the comparison indicates the ratios differing from the reference values to indicate a change in color of the fluid, and said container is arranged to carry flowing or stationary milk or the product derived from milk.

2. The arrangement as claimed in claim 1, further comprising:

a controller operatively connected to transmit data to the processor of the color sensor, the controller including a database storing data relating to previous fluid samples, and wherein the reference values are based on the data related to the previous fluid samples.

3. The system as claimed in claim 1, wherein,
the fluid is milk,
the color sensor (40) further comprises a printed circuit board (430),
the white light emitter (410) and detector (420) are arranged on a same first side of the printed circuit board (430), and
the white light emitter (410) is an LED.

4. The system as claimed in claim 3, wherein the detector comprises an array of detecting elements (421), the array including at least one detecting element arranged to detect red light and comprises a red filter, at least one detecting element arranged to detect green light and comprises a green filter, at least one detecting element arranged to detect blue light and comprises a blue filter, and at least one detecting element arranged to detect white light.

5. The system as claimed in claim 4, wherein,
the detector further includes i) at least one amplifier arranged to amplify the signal received from each detecting element, ii) at least one integrator arranged to integrate the signal received from each detecting element, and iii) at least one analog-to-digital converter arranged to digitize the signal received from each detecting element, and
the processor is arranged to modify a dynamic range of the detector (420) by varying at least one of i) an amplification of the at least one amplifier and ii) an integration time of the at least one integrator.

6. The system as claimed in claim 4, wherein the container is a milk flow meter and the detector detects the reflected light with the milk flowing through the container.

7. The system as claimed in claim 6, in combination with a plurality of teat cups for connecting to the teats of an animal, at least one milk line for transporting milk from the at least one of the teat cups to a storage container, the milk meter (30) connected to the milk line (20), the controller operatively connected to the processor of the color sensor, the controller including a database storing data relating to previous fluid samples, the controller (80) arranged to control a milk separation mechanism to separate milk in response to the signal generated by the processor when the result of the comparison indicates that the ratios differ from the reference values.

8. The system as claimed in claim 7, further in combination with an animal identification unit (90) that communicates with the controller (80), wherein the controller further stores data relating to each identified animal including data relating to the color of milk from each identified animal.

9. The system as claimed in claim 3, wherein a temperature sensor (450) is arranged on the first side of the printed circuit board (430), the temperature sensor (450) positioned for measuring ambient temperature around the white light emitter (410) and the detector (420).

10. The system as claimed in claim 1, wherein,
the white light emitter (410) is an LED,
the detector comprises an array of detecting elements, the array including a first detecting element configured to detect red light, a second detecting element configured to detect green light, a third detecting element configured to detect blue light, and a fourth detecting element that detects white light, and
each of the first, second, third, and fourth detecting elements is positioned adjacent another of the first, second, third, and fourth detecting elements.

11. The system as claimed in claim 10, wherein,
the array of detecting elements comprises plural adjacent sets of the first, second, third, and fourth detecting elements, and
the first detecting element comprises a red filter,
the second detecting element comprises a green filter,
the third detecting element comprises a blue filter, and
the fourth detecting element is a photodiode.

12. The system as claimed in claim 11, wherein at least the first and fourth detecting elements that respectively detect red and white light each further comprise an infrared filter.

13. A method for detecting color variations in a fluid comprising the steps of:
using a color sensor (40) to detect color variations in a fluid carried by a container arranged to carry flowing or stationary milk or a product derived from milk, the color sensor including i) a white light emitter (410) that emits white light into the container and into the fluid carried in the container such that the white light illuminates the fluid and is reflected off the fluid, ii) a detector (420) that detects the reflected light from the fluid and generates signals respectively representing a detected intensity of red light, blue light, green light and white light, and iii) a processor (440) connected to receive the signals respectively representing the detected intensity of the red light, the blue light, the green light and the white light from the detector (420), to calculate values representing a) a ratio of detected red light to detected white light, b) a ratio of detected blue light to detected white light, and c) a ratio of detected green light to detected white light, to compare each ratio with a corresponding reference value, and to generate a signal when a result of the comparison indicates that the ratios differ from the reference values;
illuminating the fluid carried by the container by having the white light emitter (410) emit white light into the container and into the fluid carried in the container, wherein the white light is reflected off the fluid as reflected light, and the fluid is milk or the product derived from milk;
using the detector (420), detecting the reflected light from the fluid and generating signals respectively representing the detected intensity of red light, blue light, green light and white light from the detected reflected light;
having the processor (440)
i) receive the signals respectively representing the detected intensity of the red light, the blue light, the green light and the white light from the detector (420),
ii) calculate the values representing a ratio of a) the detected red light to the detected white light, b) the ratio of detected blue light to the detected white light, and c) the ratio of detected green light to the detected white light,
iii) compare each ratio with the corresponding reference value to generate a signal when a result of the comparison indicates that the ratios differing from the reference values to indicate a change in color of the fluid.

14. The method of claim 13, wherein the fluid is milk.

15. The method of claim 13, wherein,
wherein the fluid from an animal, and the reference values are based on previous fluid samples from the animal,
the step of comparing the ratios includes comparing the ratios with respective corresponding reference ranges, and
the step of generating the signal includes generating the signal when one of the ratio falls outside of the corresponding reference range.

16. The method as claimed in claim 13, further including the step of connecting teat cups (10) to the teats of an animal and milking the animal, wherein the illuminating step includes illuminating milk carried by one or more milk tubes (20) connected to the teat cups and further including the step of automatically discarding milk when the comparison step indicates that the ratios differ from the reference values.

17. The method as claimed in claim 16, further including the step of obtaining a unique identity for each animal and storing data on the results of the comparison step in conjunction with the unique identity.

18. A system that detects color changes in a flowing fluid comprised of flowing milk or a flowing product derived from milk, comprising:
a container arranged to carry flowing or stationary milk or the product derived from milk;
a color sensor (40) that detects fluid color within the container (30) that carries flowing fluid, wherein the color sensor includes
i) a white light emitter (410) that emits white light into the container and into the fluid in the container, wherein the white light illuminates the fluid and is reflected off the fluid as reflected light,
ii) a detector (420) that detects the reflected light and generates signals respectively representing a detected intensity of red light, blue light, green light, and white light from the detected reflected light, and
iii) a processor (440)
connected to receive the signals respectively representing the detected intensity of red light, blue light, green light, and white light,
calculate values representing a) a ratio of detected red light to detected white light, b) a ratio of detected blue light to detected white light, and c) a ratio of detected green light to detected white light, and
compare each said calculated ratio with a corresponding reference value, and to generate a signal when a result of the comparison indicates that the ratios differ from the reference values to indicate a change in color of the flowing fluid.

19. The arrangement as claimed in claim 18, further comprising:
a controller operatively connected to transmit data to the processor of the color sensor, the controller including a database storing data relating to previous samples of the fluid,
wherein the fluid is milk, and
wherein the reference values are based on the data related to the previous samples.

20. The system as claimed in claim 19, wherein,
the emitter (410) and detector (420) are arranged facing the container,
the white light emitter (410) is an LED,
the detector comprises an array of detecting elements, the array including a first detecting element configured to detect red light, a second detecting element configured to detect green light, a third detecting element configured to detect blue light, and a fourth detecting element that detects white light,
each of the first, second, third, and fourth detecting elements is positioned adjacent another of the first, second, third, and fourth detecting elements,
the array of detecting elements comprises plural adjacent sets of the first, second, third, and fourth detecting elements, where the first detecting element comprises a red filter, the second detecting element comprises a green filter, the third detecting element comprises a blue filter, and the fourth detecting element is a photodiode, the detector further includes i) at least one amplifier arranged to amplify the signal received from each detecting element, ii) at least one integrator arranged to integrate the signal received from each detecting element, and iii) at least one analog-to-digital converter arranged to digitize the signal received from each detecting element, and the processor is further arranged to modify a dynamic range of the detector (420) by varying at least one of i) an amplification of the at least one amplifier and ii) an integration time of the at least one integrator.

* * * * *